(12) United States Patent
Hantash et al.

(10) Patent No.: US 7,585,626 B1
(45) Date of Patent: Sep. 8, 2009

(54) METHODS FOR NUCLEIC ACID AMPLIFICATION

(75) Inventors: Feras Hantash, Mission Viejo, CA (US); Jennifer Dianne Keen-Kim, Playa Vista, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 85 days.

(21) Appl. No.: 10/921,482

(22) Filed: Aug. 19, 2004

(51) Int. Cl.
*C12Q 1/68* (2006.01)
*C12P 19/34* (2006.01)

(52) U.S. Cl. .................... 435/6; 435/91.1; 435/91.2

(58) Field of Classification Search ............... None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 5,242,796 A | 9/1993 | Prober et al. | |
| 5,492,817 A * | 2/1996 | Thompson et al. | 435/68.1 |
| 5,512,441 A * | 4/1996 | Ronai | 435/6 |
| 5,612,179 A | 3/1997 | Simons | |
| 5,932,451 A * | 8/1999 | Wang et al. | 435/91.21 |
| 6,103,465 A | 8/2000 | Johnston-Dow et al. | |
| 6,124,120 A * | 9/2000 | Lizardi | 435/91.2 |
| 6,270,967 B1 | 8/2001 | Whitcombe et al. | |
| 6,537,757 B1 | 3/2003 | Langmore et al. | |
| 6,579,704 B2 | 6/2003 | Short | |

OTHER PUBLICATIONS

Norgaard et al. (Sequencing-based typing of HLA-A locus using mRNA and a single locus-specific PCR followed by cycle-sequencing with AmpliTaq DNA polymerase, FS. Tissue Antigens. May 1997;49(5):455-65).*

Takeda et al. ("Recessive inheritance of thyroid hormone resistance caused by complete deletion of the protein-coding region of the thyroid hormone receptor-beta gene" J Clin Endocrinol Metab. Jan. 1992;74(1):49-55).*

Milunksy et al. ("Novel mutations and the emergence of a common mutation in the SDHD gene causing familial paraganglioma" Am J Med Genet. May 15, 2001;100(4):311-4).*

Astuti et al. ("Gene mutations in the succinate dehydrogenase subunit SDHB cause susceptibility to familial pheochromocytoma and to familial paraganglioma" Am J Hum Genet. Jul. 2001;69(1):49-54. Epub Jun. 12, 2001).*

Glick et al. ("Chemical Synthesis, Sequencing, and Amplification of DNA" Molecular Biotechnology: Principles and Applications of Recombinant DNA. 1998 Sec. Ed., p. 92).*

(Continued)

*Primary Examiner*—Kenneth R. Horlick
*Assistant Examiner*—Christopher M. Babic
(74) *Attorney, Agent, or Firm*—Foley & Lardner LLP (57) ABSTRACT

Disclosed are methods for amplifying and sequencing target segments of nucleotides. In the method, nucleic acids are amplified using at least two oligonucleotide primers, wherein at least one of the primers contains a complimentary region that hybridizes adjacent to the target segment of nucleotides and an extender region that includes a primer hybridization sequence. Also included are methods of amplification with an extender region includes a sequence encoding a promoter for an RNA polymerase and optionally sequences for translation. The latter amplified products may be used for transcription of a RNA including subsequent translation of the RNA to generate a protein product.

51 Claims, 1 Drawing Sheet

OTHER PUBLICATIONS

University of Michigan Sequencing Core (http://seqcore.brcf.med.umich.edu/doc/dnaseq/primers.html.*

Williams (Optimization strategies for the polymerase chain reaction Biotechniques. Jul.-Aug. 1989;7(7):762-9).*

Chen et al. ("A microsphere-based assay for multiplexed single nucleotide polymorphism analysis using single base chain extension" Genome Res. Apr. 2000;10(4):549-57).*

Sasaki et al. ("Transcriptional sequencing: A method for DNA sequencing using RNA polymerase" Proc Natl Acad Sci U S A. Mar. 31, 1998;95(7):3455-60).*

Ansorge et al., "A Non-Radioactive Automated Method for DNA Sequence Determination" *J. Biochem. Biophys. Meth.* 13:315-323 (1986).

Asteria et al., "Prenatal Diagnosis of Thyroid Hormone Resistance" *J. of Clin. Endocrinology & Metabolism* 84:405-410 (1999).

Beck, et al., "Chemiluminescent Detection of DNA: Application for DNA Sequencing and Hybridization" *Nucleic Acids Res.* 17:5115-5123 (1989).

Beck, S., "Colorimetric-Detected DNA Sequencing" *Analytical Biochem.* 164:514-520 (1987).

Dolnik, V., "DNA Sequencing by Capillary Electophoresis (Review)" *J. Biochem. Biophys. Methods* 41:103-119 (1999).

Dovichi and Zhang, "DNA Sequencing by Capillary Array Electrophoresis" *Meth. in Molecular Biol.* 167:225-239 (2001).

Hafner, et al., "Isothermal Amplification and Multimerization of DNA by Bst DNA Polymerase" *BioTechniques* 30:852-867 (2001).

Heller, C., "Principles of DNA Separation with Capillary Electrophoresis" *Electrophoresis* 22:629-643 (2001).

Kambara, et al., "Optimization of Parameters in a DNA Sequenator Using Fluorescence Detection" *BioTechnology* 6:816-821 (1988).

Lingappa, et al., "A Eukaryotic Cytosolic Chaperonin is Associated With A High Molecular Weight Intermediate in the Assembly of Hepatitis B Virus Capsid, a Multimeric Particle" *J. of Cell Biol.* 125:99-111 (1994).

Maxam and Gilbert, "Sequencing End-Labeled DNA with Base-Specific Chemical Cleavages" *Methods in Enzymology* 65:499-559 (1980).

Mitchelson, K., "The Application of Capillary Electrophoresis for DNA Polymorphism Analysis" *Meth. in Molec. Biol.* 162:3-26 (2001).

Oberste, et al., "Comparison of Classic and Molecular Approaches for the Identification of Untypeable Enteroviruses" *J. of Clin. Microbiol.* 38:1170-1174 (2000).

Oberste, et al., "Typing of Human Enteroviruses by Partial Sequencing of VP1" *J. of Clin. Microbiol.* 37:1288-1293 (1999).

Safer, et al., "Defective Release of Corepressor by Hinge Mutants of the Thyroid Hormone Receptor Found in Patients with Resistance to Thyroid Hormone" *J. of Biol. Chem.* 273:30175-30182 (1998).

Safer, et al., "The Thyroid Hormone Receptor-β Gene Mutation R383H is Associated with Isolated Central Resistance to Thyroid Hormone" *J. of Clin. Endoc. & Metab.* 84:3099-3109 (1999).

Saiki, R., "Amplification of Genomic DNA" *PCR Protocols: A Guide to Methods and Application* pp. 13-20 (1990).

Sanger, et al., "DNA Sequencing with Chain-Terminating Inhibitors" *Proc. Natl. Acad. Sci. USA* 74:5463-5467 (1977).

Smith, et al., "The Synthesis of Oligonucleotides Containing an Aliphatic Group at the 5' Terminus: Synthesis of Fluorescent DNA Primers for Use in DNA Sequence Analysis" *Nucleic Acids Research* 13:2399-2412 (1985).

Takeda, et al., "Screening of Nineteen Unrelated Families with Generalized Resistance to Thyroid Hormone for Known Point Mutations in the Thyroid Hormone Receptor β Gene and the Detection of a New Mutation" *J. Clin. Invest.* 87:496-502 (1991).

Wharam, et al., "Specific Detection of DNA and RNA Targets Using a Novel Isothermal Nucleic Acid Amplification Assay Based on the Formation of a Three-Way Junction Structure" *Nucleic Acids Res.* 29:1-8 (2001).

Yu, et al., "Tailed Primer Base Excision Sequence Scanning (TP-BESS) for Detection of Single Nucleotide Polymorphisms (SNPs)" *Plant Molecular Biology Reporter* 19:49-54 (2001).

* cited by examiner

FIG. 1

METHODS FOR NUCLEIC ACID AMPLIFICATION

FIELD OF THE INVENTION

The present invention relates to the analysis of nucleic acids. In a particular aspect, the invention relates to the amplification of nucleic acid and/or sequencing.

BACKGROUND OF THE INVENTION

Nucleotide sequencing methods are valuable for molecular biological investigations. The development of rapid and reliable nucleotide sequencing methods has led to great advances in the understanding of the organization of genetic information and has laid the foundation for the detailed analysis of the structure and function of genes.

Two general methods used to sequence DNA include the Maxam-Gilbert chemical degradation method (A. M. Maxam et al., Methods in Enzymology 65, 499-559 (1980)) and the Sanger dideoxy chain termination method (F. Sanger, et al., Proc. Natl. Acad. Sci. USA 74, 5463-5467 (1977)). Both of these techniques are detailed in Molecular Cloning: A Laboratory Manual (Sambrook, Fritsch, Maniatis, eds., Cold Spring Harbor Laboratory Press, 1989).

With the Maxam-Gilbert technique, DNA fragments are prepared through base-specific chemical cleavage of the piece of DNA to be sequenced. The piece of DNA to be sequenced is first 5'-end-labeled with $^{32}$P and then divided into four portions. Each portion is subjected to a different set of chemical treatments designed to cleave DNA at positions adjacent to a given base (or bases). The result is that all labeled fragments will have the same 5'-terminus as the original piece of DNA and will have 3'-termini defined by the positions of cleavage. This treatment is performed under conditions that generate DNA fragments of convenient lengths for separation by gel electrophoresis.

With the Sanger technique, DNA fragments are produced through partial enzymatic copying (i.e., synthesis) of the piece of DNA to be sequenced. In this method, the piece of DNA to be sequenced may be inserted, using standard techniques, into a "sequencing vector", a large circular, single-stranded piece of DNA such as the bacteriophage M13. This becomes the template for the copying process. Alternatively, instead of using a sequencing vector, polymerase chain reaction (PCR) can be used to produce templates directly from genomic DNA, eliminating the need for cloning. A short piece of DNA with a sequence complementary to a region of the template just upstream from the region to be sequenced is annealed to the template and serves as a primer for the synthesis. In the presence of the four natural deoxyribonucleoside triphosphates (dNTP's), a DNA polymerase will extend the primer from the 3'-end to produce a complementary copy of the template. To produce a complete set of sequencing fragments, four reactions are run in parallel, each containing the four dNTP's along with a single dideoxyribonucleoside triphosphate (ddNTP) terminator, one for each base. $^{32}$P-labeled or fluorophore-labeled dNTP or ddNTP is added to afford labeled fragments. If a dNTP is incorporated by the polymerase, chain extension can continue. If the corresponding ddNTP is selected, the chain is terminated. The ratio of ddNTP to dNTP is adjusted to generate DNA fragments of appropriate lengths. Each of the four reaction mixtures will, thus, contain a distribution of fragments with the same dideoxynucleoside residue at the 3'-terminus and a primer-defined 5' terminus. In some modern methods, the four reactions are combined into a single reaction by labeling the four ddNTPs with different color fluorophores. When the product of this reaction is separated by capillary electrophoresis, the individual fragments are distinguished by size and color.

Fragments generated utilizing the Sanger method of sequencing may be end-labeled, via, for example, the utilization of primers having labeled nucleotides incorporated into their sequence. Alternatively, molecules may be end-labeled via the utilization of labeled dideoxynucleosides or other modified chain-terminating nucleotides or nucleotide mimics. Molecules can also be labeled internally by the utilization of one or more labeled nucleotides incorporated during the synthesis step of the process.

In both the Sanger and Maxam-Gilbert methods, base sequence information, which generally cannot be directly determined by physical methods, is converted into chain-length information, which can be determined. This determination can be accomplished through electrophoretic separation. Under denaturing conditions (e.g., high temperature, presence of urea, etc.), short DNA fragments migrate as if they were stiff rods. If a gel matrix is employed for the electrophoresis, the DNA fragments are sorted by size. The single-base resolution required for sequencing can usually be obtained for DNA fragments containing up to several hundred bases. To determine a full sequence, the four sets of fragments produced by either Maxam-Gilbert or Sanger methodology are subjected to electrophoresis. This results in the fragments being spatially resolved along the length of the gel.

Dyes such as, for example, infrared dyes, fluorescent dyes, colorimetric dyes, chemiluminescent dyes, and/or other detectable molecules, can be used instead of the $^{32}$P label in the foregoing sequencing reactions. Molecules other than dideoxynucleotides may also be used as chain terminators in these reactions.

One method of discriminating dyes in these types of reactions is described in U.S. Pat. No. 5,242,796 entitled "Method, System, and Reagents for DNA Sequencing". This system is available from E.I. Du Pont de Nemours and Company (Wilmington, Del.), and is known as the Genesis 2000. The system detects the presence of radiant energy from closely-related yet distinguishable reporters or labels that are covalently attached to compounds which function as chain-terminating nucleotides in a modified Sanger DNA chain-elongation method. Distinguishable fluorescent reporters are attached to each of the four dideoxynucleotide bases represented in Sanger DNA-sequencing reactions, i.e., dideoxynucleotides of adenine (A), guanine (G), cytosine (C), and thymine (T). These reporter-labeled chain-terminating reagents are substituted for unlabeled chain terminators in the traditional Sanger method and are combined in reactions with the corresponding deoxynucleotides, an appropriate primer, template, and polymerase. The resulting mixture contains DNA fragments of varying length that differ from each other by one base and terminate on the 3'-end with uniquely labeled chain terminators corresponding to one of the four DNA bases. This labeling method allows elimination of the customary radioactive label contained in one of the deoxynucleotides of the traditional Sanger method.

Detection of these reporter labels can be accomplished with two stationary photomultiplier tubes (PMT's) that receive differing wavelength bands of fluorescent emissions from laser-stimulated reporters attached to chain terminators on the DNA fragments. These fragments can be electrophoretically separated in space and/or time to move along an axis perpendicular to the sensing area of the PMT's. The fluorescent emissions first pass through a dichroic or other wavelength-selective filter or filters, placed so as to direct one characteristic wavelength to one PMT and the other characteristic wavelength to the other PMT. In this manner, different digital signals are created in each PMT that can be ratioed to produce a third signal that is unique to a given fluorescent reporter, even if a series of fluorescent reporters have closely-spaced emission wavelengths. This system is capable of detecting reporters with efficiently-spaced emissions whose maxima differ by only 5 to 7 nm. Therefore, the sequential base assignments in a DNA strand of interest can be made on the basis of the unique ratio derived for each of the four reporter-labeled chain terminators which correspond to each of the four bases in DNA. Although the base information in the Genesis system is contained in fluorescent labels, the information may also be contained in colorimetric labels (S. Beck, Anal. Biochem. 164(2), 514-520 (1987)), chemiluminescent labels (S. Beck Nucleic Acids Research 17, 5115-5123 (1989)), or other labels.

The Genesis DNA sequencer is designed to take advantage of the dideoxy chain termination chemistry. In order to employ this chemistry, it is necessary to use four chemically-similar dyes to distinguish the four bases, A, C, G, and T. Unless the dyes are carefully chosen and exhaustively evaluated, their electrophoretic mobility may differ in some DNA sequences, leading to a scrambling of sequence information. The four dyes, chosen for similar electrophoretic mobility, have overlapping emission and excitation spectra. The need to distinguish these dyes without the excessive light loss of extremely narrow-band filters led to a two-channel detection scheme in which the ratio of two signals is used to determine which base has passed the detector. When peaks are well-resolved and noise-free, the ratiometric signals are easy to interpret. However, to maximize the amount of sequence information that can be obtained from each run, it is necessary to accurately interpret the two-channel signal under conditions of poor peak resolution and significant noise.

Sequencers employing primer chemistry have also been described (L. M. Smith, et al., Nucleic Acids Research 13, 2399-2412 (1985), and W. Ansorge, et al., J. Biochem. Biophys. Meth. 13, 315-323 (1986)). These sequencers employ four channels, one for each base. Other sequencers, such as that described by Kambara, et al., Biotechnology 6, 816-821 (1988), employ one signal in each of four electrophoresis lanes. These systems employ yet another class of data analysis methods, since the results from four separate lanes must be registered or aligned in the proper time sequence.

Although the advancements of nucleotide sequencing methods have led to an expansion of useful applications of nucleotide sequencing technology, certain limitations remain. For example, regions of a genome that are repetitive, assume a secondary, tertiary or quaternary structure or have polymorphic regions may be difficult to sequence. Moreover, it may be difficult or impossible to sequence a region of a genome that is near or adjacent to difficult to sequence regions using certain sequencing techniques. Also, using dye-termination sequencing protocols, the first 50 nucleotides or so do not provide useful sequence results, making it difficult or impossible to sequence short nucleotide segments. For many applications of genomic sequencing difficult to sequence regions may be ignored or omitted from a particular study. In clinical diagnostics, however, the ability to obtain the sequence of a particular nucleotide segment may have great clinical value. Thus, methods that improve the ability to obtain nucleotide sequences in or around difficult to sequence genomic regions are desired.

SUMMARY OF THE INVENTION

It is an object of the present invention to provide methods to amplify a target segment of nucleotides in a nucleic acid and to determine the sequence of the amplified nucleotides. Common to the methods is the use of at least one primer which includes a complementary region that hybridizes adjacent to the target segment of nucleotides and further includes an extender region that has a nucleotide sequence that is different from the complementary region and does not hybridize to the target segment of nucleotides.

In some embodiments, the extender region includes a primer hybridization sequence which may be a target for a DNA polymerase used for sequencing. In other embodiments, the extender region is not fully complementary or is not complementary to the segment of nucleotides adjacent to which the complementary region of the primer hybridizes in the target nucleic acids. In yet other embodiments, the extender region does not hybridize under stringent conditions to any nucleic acids in a test sample. In further embodiments, the extender region is not subjected to cleavage by restriction enzymes.

In one aspect, a method for sequencing is provided involving the following steps:
(a) amplifying the target segment of nucleotides using at least two oligonucleotide primers that flank the target sequence, wherein at least one of the oligonucleotide primers comprise:
   i) a complementary region that hybridizes adjacent to the target segment of nucleotides; and
   ii) an extender region that includes a primer hybridization sequence wherein said extender region does not hybridize to the target segment of nucleotides and said extender region is not fully complementary to the segment of nucleotides adjacent to which the complementary region of the primer hybridizes in the target nucleic acids, with a proviso that the length of the complimentary region and the extender region excluding the primer hybridization sequence together represents a contiguous segment of at least about 50 nucleotides; and
(b) determining the sequence of the amplified target segment by priming with an oligonucleotide primer that is complementary to said primer hybridization sequence of the extender region.

In another aspect, a method for amplifying a target segment of nucleotides in a nucleic acid test sample is provided. The target segment is less than about 150 nucleotides in length and is located less than 100 nucleotides from a genomic region that functions as a primer hybridization/extension barrier. Such genomic region can be a repetitive element, nucleic acid secondary or tertiary structure, AT-rich region, GC-rich region or a polymorphic region. In this method, the complementary region of the primer is designed to hybridize between the target sequence and the genomic region primer hybridization/extension barrier. The method involves the following steps:
(a) contacting the nucleic acids in the test sample with at least two oligonucleotide primers that flank the target segment of nucleotides, wherein at least one of the oligonucleotide primers comprise:
   i) a complementary region that hybridizes adjacent to the target segment of nucleotides; and ii) an extender region that includes a primer hybridization sequence wherein the extender region does not hybridize to the target segment of nucleotides and the extender region is not fully complementary to the segment of nucleotides adjacent to which the complementary region of the primer hybridizes in the target nucleic acids, with a proviso that the length of the complimentary region and the extender region excluding the primer hybridization sequence together represents a contiguous segment of at least 50 nucleotides; and (b) amplifying the target segment of nucleotides by priming with the primers.

In a third aspect, a method for amplifying a target segment of nucleotides in a nucleic acid test sample for transcription of the amplified target segment is provided. The target segment is less than about 150 nucleotides in length and is located less than 100 nucleotides from a genomic region that functions as a primer hybridization/extension barrier. Such genomic region can be a repetitive element, nucleic acid secondary or tertiary structure, AT-rich region, GC-rich region or a polymorphic region. In this method, the complementary region of the primer is designed to hybridize between the target sequence and the genomic region primer hybridization/extension barrier. The method involves the following steps:

(a) contacting the nucleic acids in the test sample with at least two oligonucleotide primers that flank the target segment of nucleotides, wherein at least one of the oligonucleotide primers comprise:

i) a complementary region that hybridizes adjacent to the target segment of nucleotides; and ii) an extender region that includes a sequence encoding a promoter for an RNA polymerase wherein the extender region does not hybridize to the target segment of nucleotides and the extender region is not fully complementary to the segment of nucleotides adjacent to which the complementary region of the primer hybridizes in the target nucleic acids, with a proviso that the length of the complimentary region and the extender region excluding the sequence encoding the promoter for an RNA polymerase together represents a contiguous segment of at least 50 nucleotides; and (b) amplifying the target segment of nucleotides by priming with the primers.

In some embodiments, the amplified target segment containing sequence for a promoter of an RNA polymerase may be used to transcribe RNA which may then be translated. In some embodiments, the extender region may include a ribosome binding site, and, if desired, translation initiation codon.

As used herein, the term "sample" or "test sample" refers to any liquid or solid material believed to comprise nucleic acids of interest. A test sample may be obtained from any biological source (i.e., a "biological sample"), such as cells in culture or a tissue sample. As used herein, the term "test nucleic acids" refers to any nucleic acids believed to contain any nucleotides of interest. As used herein, the term "target segment" refers to any portion of nucleotides of interest in a sample of nucleic acids.

As used herein, the term "nucleotide sequencing" refers to the determination or identity of the order of nucleotides present in a nucleic acid.

As used herein, the term "repetitive elements" refers to a segment of a nucleic acid that contains a repeated sequence of nucleotides. Repetitive elements can include single nucleotide repeats (e.g., AAA), di-nucleotide repeats (e.g., ATAT or AGAG) tri-nucleotide repeats, tetranucleotide repeats, telomeric repetitive elements and the like. Repetitive elements may also include repeats including, but not limited to ALU, LINE, SINE, L, and P elements.

As used herein, the term "GC-rich region" refers to a segment of a nucleic acid wherein at least 55% of the bases, preferably at least 65%, more preferably at least 75%, most preferably at least 85% of the bases comprise a guanine or a cytosine nucleotide. As used herein, the term "AT-rich region" refers to a region of a nucleic acid wherein at least 55% of the bases, preferably at least 65%, more preferably at least 75%, most preferably at least 85% of the bases comprise an adenine or a thymine nucleotide.

As used herein, the term "polymorphic region" refers to a segment of a nucleic acid which has sequence variation among individuals in a population. For example, a polymorphic region is a segment of nucleic acid where allelic variation arises.

As used herein, the term "primer hybridization/extension barrier" is used to refer to a genomic region that interferes with the process of primer hybridization and/or extension involved in amplification and nucleotide sequencing. Such barriers involve a genomic region that is upstream or downstream of the target segment of nucleotides. Examples of a genomic region which constitute primer hybridization/extension barriers include regions with repetitive elements, regions that can assume secondary, tertiary or quaternary structures, GC-rich regions, AT-rich regions, polymorphic regions, and the like. The genomic region primer hybridization/extension barrier acts to interfere with sequencing when a primer extension sequencing reaction necessarily extends into and past the barrier in order to reach the target segment of nucleotides sought to be sequenced or acts to interfere with sequencing when the amplification primer is unable to hybridize. A genomic region primer hybridization/extension barrier may completely interfere or only partially interfere with amplification and/or sequencing.

The term "amplify" with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860.

As used herein, the terms "complementary" or "complementarity" are used in reference to polynucleotides (i.e., a sequence of nucleotides such as an oligonucleotide or a target nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association". For example, for the sequence "5'-A-G-T-3'" is complementary to the sequence "3'-T-C-A-5". Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementary may be "partial" in which only some of the nucleotide bases of two nucleic acid strands are matched according to the base pairing rules. Complementary may be "complete" or "total" where all of the nucleotide bases of two nucleic acid strands are matched according to the base pairing rules. Complementary may be absent where none of the nucleotide bases of two nucleic acid strands are matched according to the base pairing rules. The degree of complementary between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementary, or lack thereof, to a nucleotide within another nucleic acid strand, in contrast or comparison to the complementary between the rest of the oligonucleotide and the nucleic acid strand.

As used herein, the term "oligonucleotide" refers to a short polymer composed of deoxyribonucleotides, ribonucleotides or any combination thereof. Oligonucleotides of the invention are at least 10 but not more than 300 nucleotides in length. The single letter code for nucleotides is as described in the U.S. Patent Office Manual of Patent Examining Procedure, section 2422, table 1. In this regard, the nucleotide designation "R" means guanine or adenine, "Y" means thymine (uracil if RNA) or cytosine; and "M" means adenine or cytosine. An oligonucleotide may be used as a primer or as a probe.

As used herein, a "primer" for amplification is an oligonucleotide that comprises a region at the 3' end ("complementary region") of the oligonucleotide that specifically hybridizes or anneals to a target nucleotide sequence (hereinafter "primer hybridization sequence"). The complimentary region of the primer can be between about 12 to about 50 nucleotides, more preferably about 12 to about 25 nucleotides, more preferably about 16 to about 23 nucleotides, most preferably about 18 to about 22 nucleotides. The skilled artisan is capable of designing and preparing primers that are appropriate for amplifying a target sequence. The length of the primer hybridization sequence of amplification primers for use in the present invention depends on several factors including the nucleotide sequence identity and the temperature at which these nucleic acids are hybridized or used during in vitro nucleic acid amplification. The considerations necessary to determine a preferred length for the primer hybridization sequence of an amplification primer of a particular sequence identity are well known to the person of ordinary skill. For example, the length of a short nucleic acid or oligonucleotide can relate to its hybridization specificity or selectivity.

In certain aspects of the present invention, oligonucleotide primers may contain an "extender region" 5' to the complementary region. The extender region has a nucleotide sequence that is different from the complementary region and the extender region does not hybridize to the target segment of nucleotides. The extender region is not fully complementary or is not complementary to the segment of nucleotides adjacent to which the complimentary region of the primer hybridizes in the target nucleic acids. In some embodiments, the extender region does not hybridize to the nucleic acids in the sample to be evaluated. The extender region may include a primer hybridization sequence. Preferably the primer hybridization sequence of the extender region occurs at or near the 5' terminus of the extender region. In certain embodiments, the length of the complimentary region and the extender region excluding the primer hybridization sequence together represents a contiguous segment of at least about 50 nucleotides, or at least about 60 nucleotides, or at least about 80 nucleotides or at least about 100 nucleotides. In some embodiments, the extender region comprises about 35 to about 100 nucleotides, about 100 to about 150 nucleotides, about 150 to about 200 nucleotides or more than about 200 nucleotides. In some embodiments the extender region may contain a sequence encoding a promoter for an RNA polymerase. In some embodiments, the extender region may also include sequences for translation of amplified fragment.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, an oligonucleotide primer is "specific" for a nucleic acid if the primer hybridization sequence of the primer has at least 50% sequence identity with a portion of the nucleic acid when the oligonucleotide and the nucleic acid are aligned. An oligonucleotide primer that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhardt's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, sequences that have "high sequence identity" have identical nucleotides at least at about 50% of aligned nucleotide positions, preferably at least at about 58% of aligned nucleotide positions, and more preferably at least at about 76% of aligned nucleotide positions.

DETAILED DESCRIPTION OF THE INVENTION

Figure 1:
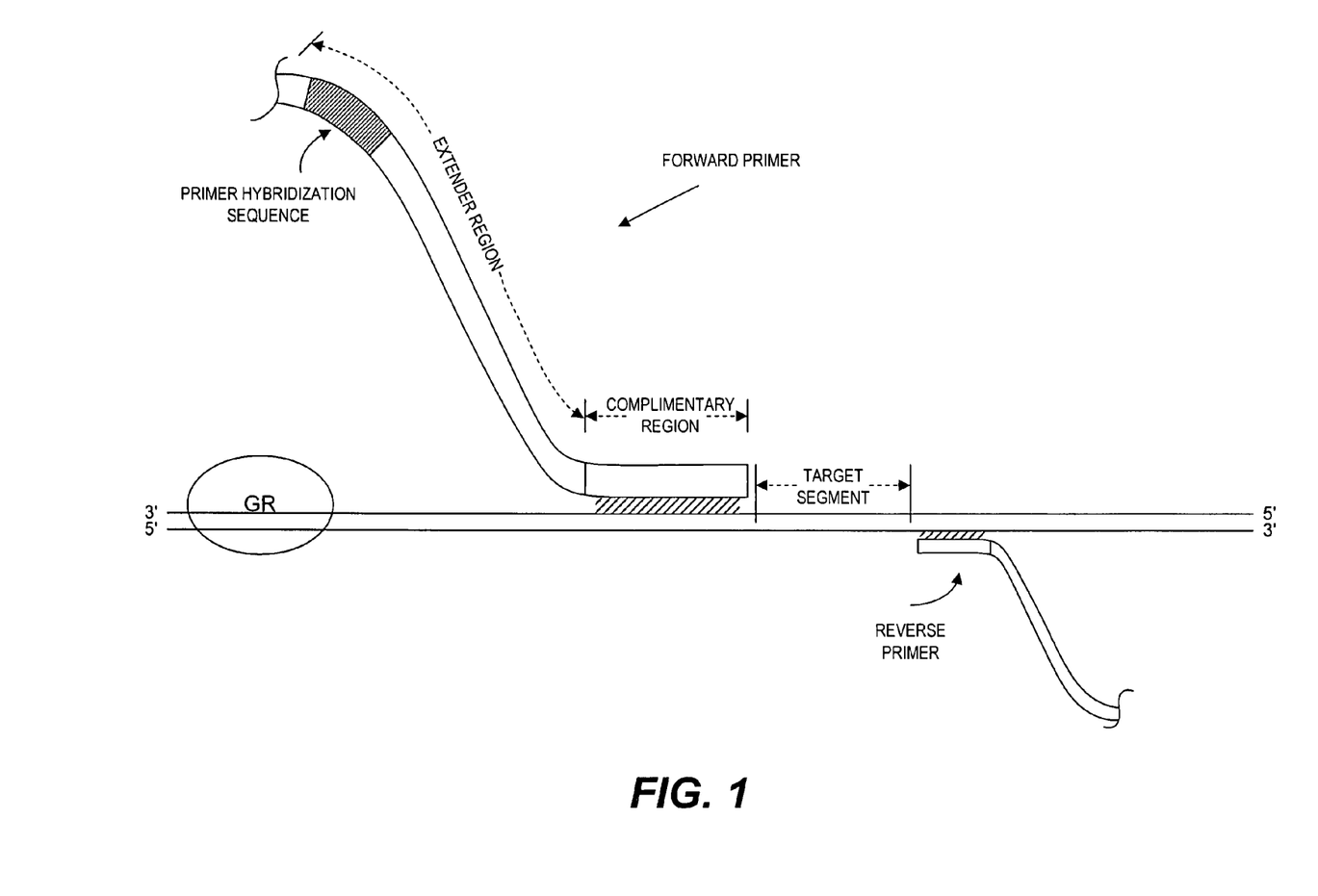
FIG. 1 is a schematic representation of one embodiment for amplification of a target segment of nucleotides. GR refers to a genomic region that functions as a barrier to primer hybridization/extension; e.g. a repetitive element, region that assumes secondary, tertiary or quaternary structure, GC-rich region, AT-rich region, or polymorphic region.

Many nucleotide sequences are difficult to sequence using traditional nucleotide sequencing methods. Furthermore, difficult nucleotide sequences that are near or adjacent to target nucleotide segments ("primer hybridization/extension barriers") interfere with the sequencing of the target segments. For example, repetitive elements can cause polymerase slippage and insertion or deletion of repeat units. The expansion and/or contraction of repeat units therefore causes difficulties in accurately amplifying or sequencing through fragments containing these repetitive elements. Centromeres and telomeres of chromosomes are often highly repetitive, thus difficult to sequence. Some sequences have the ability to assume a secondary or tertiary structure, which can hinder PCR amplification and/or sequencing. Such structures may include loops, bulges, stem-loop structures and triplex DNA. Models and software are available that can be used to predict sequences that may form secondary structures. Further, regions of DNA that form quaternary structures (i.e. regions of nucleic acid interacting with other elements, such as other strands of nucleic acid) can also hinder PCR amplification and/or sequencing. GC-rich sequences can be difficult to amplify and/or sequence because the three hydrogen bonds between guanine and cytosine bases create a tighter bond than the 2 hydrogen bonds between adenine and thymine. Long stretches of G's and C's require more force to pull the strands apart and therefore have higher melting temperatures. GC-rich sequences can cause slippage during polymerization and often lead to poor quality sequencing results. Likewise AT-rich sequences can often cause poor sequencing results. Highly polymorphic regions also cause difficulties in DNA sequencing. For example, a polymorphism associated with a PCR or sequencing site can cause the amplification to fail, often called allele drop-out. Genomic regions that commonly have insertions or deletions can also make sequencing difficult. Heterozygous small insertions or deletions can result in overlapping signals by dye-terminator sequencing procedures.

A limitation of dye-terminator sequencing is that the first about 50 or so nucleotides of sequence usually do not provide useful sequencing results. Therefore, if a relatively small target segment occurs on a region of a genome that is near or adjacent to a region of the genome that contains a primer hybridization/extension barrier, it may be particularly difficult to amplify and/or sequence the target segment of interest.

The present invention overcomes these problems through the design of an extender region in an amplification primer. By placing a primer hybridization sequence at the far end of the extender region, the resulting amplicon contains a significant run of nucleotides upstream of the target segment to be sequenced. This run of nucleotides representing the spacing between the primer hybridization sequence and the target segment enables the sequencing reaction to achieve high fidelity by the time the polymerase reaches the target sequence, therefore enabling the identification of the sequence at the start of the target segment that ordinarily would have been unreadable.

Amplification of the target segment of nucleotides can be achieved using one or more primers that contain an extender region. In certain embodiments, two of the amplification primers contain the extender and complimentary regions. In such cases, the sequence of the two extender regions may differ. In other embodiments, a pair of amplification primers may be used, one primer containing an extender region and a complimentary region and another primer lacking an extender region.

As discussed, the extender region may comprise a primer hybridization sequence. Preferably, a primer hybridization sequence is at or near the 5' terminus of the extender region. The distance between the primer hybridization sequence of the extender region and the 3' end of the complementary region can vary. The distance may be at least 30, or at least 40, or at least 50, or at least 60 nucleotides in length.

The primer hybridization sequence may be complimentary to a primer commonly used for sequencing reactions. Such "universal sequencing primers" include, for example, those of T7, T7 promoter, T7 terminator, T3, T3 promoter, M13, M13 forward (M13F), M13 reverse (M13R), and SP6. In some embodiments the extender region may contain a restriction enzyme recognition site.

The length of the complimentary region and the extender region (excluding the primer hybridization sequence) can vary. In some embodiments, this length represents a contiguous segment of at least 50 nucleotides, or at least 60 nucleotides, or at least 80 nucleotides or at least 100 nucleotides.

The amplification and sequencing methods disclosed herein may be performed using any sample comprising nucleic acids. Biological samples may be obtained by standard procedures and may be used immediately or stored (e.g., the sample may be frozen at about −20° C. to about −80° C.) for later use. Nucleic acids may be isolated and/or purified or extracted from biological samples. Various commercial nucleic acid purification kits, such as QIAmp 96 Virus BioRobot Kit and Qiagen's BioRobot 9604 are known to the skilled artisan Amplification of a target segment of nucleotides using primers described herein can be performed by any of various methods known to the skilled artisan. For example, "polymerase chain reaction" ("PCR"), the method of K. B. Mullis U.S. Pat. Nos. 4,683,195 and 4,683,202, for increasing the concentration of a segment of a template sequence in a mixture of genomic DNA without cloning or purification may be used for amplification of nucleic acids. With PCR, it is possible to amplify a single copy of a specific template sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplicons prepared using the methods of the invention can vary in size. In some embodiments, the amplicon is at least about 75 nucleotides in length, or at least about 100 nucleotides, or at least about 150 nucleotides, or at least about 200 nucleotides or at least about 250 nucleotides in length.

In certain embodiments, the amplicons prepared as described herein may be sequenced directly, i.e., without digestion by restriction enzymes and without the need to subclone the amplicon into a vector, for example, a plasmid sequencing vector.

The target segment of nucleotides that is amplified and/or sequenced using the methods described herein can be 1 to about 10 nucleotides in length, about 10 to about 50 nucleotides in length, about 50 to about 100 nucleotides in length, about 100 to about 150 nucleotides in length, about 150 to 200 nucleotides in length, or at least about 200 nucleotides in length. In other embodiments, the amplicon for sequencing is at least about 150 nucleotides, at least about 200 nucleotides, or at least about 250 nucleotides in length and comprises a target segment that is about 1 to about 100 nucleotides, about 1 to about 75 nucleotides, about 1 to about 50 nucleotides, or about 1 to about 25 nucleotides in length.

The methods may be used to sequence a target segment that is flanked by a genomic region that comprises a primer hybridization/extension barrier. In some embodiments, the target segments is less than 200 nucleotides, less than 100 nucleotides, less than 50 nucleotides, or less than 20 nucleotides away from the primer hybridization/extension barrier. In certain embodiments, the target segment is a complete exon. In other embodiments, the target segment is a portion (i.e. subfragment) of a complete exon.

Sequencing may be carried out using any techniques known by those skilled in the art, including but not limited to Maxam-Gilbert sequencing, Sanger sequencing, and, more preferably, fluorescent sequencing. For example the nucleic acids may sequenced using a dye termination protocol. In the first type of reaction using dye-labeled termination nucleotides, fluorescent dye-labeled dideoxy nucleotides are incorporated into a sequence during the extension phase, which may be the extension phase of a PCR cycle. When a dye-labeled dideoxy nucleotide is introduced into the sequence during this phase of the reaction, the extension of the DNA product stops. Termination occurs because the dye-labeled termination nucleotide lacks a 3' hydroxyl group and is incapable of being extended. This type of sequencing reaction will produce a number of different size fragments all containing a dye-labeled dideoxy nucleotide at the end of the fragment. The number of different size fragments will be equal to the number of bases in the sequence. This type of reaction uses different fluorescent dyes used in cycle sequencing, each one associated with a specific nucleotide (e.g., A, C, G, T or U). As such, the sequencing reaction may be performed in a single tube. The products can be visualized and identified by migration through a gel (e.g., by performing PAGE) followed by analysis using an apparatus that incorporates a scanning excitation laser. As the excitation laser scans along the electrophoretic axis of the gel, it excites and detects the emission from each dye (i.e., tag) at each cycle sequencing termination point within the gel.

Sequencing protocols may also make use of fluorescent dye labeled primers. However, identical primers that are distinctly labeled with four separate dyes, corresponding to A, C, G, and T, must be used in this case. After the sequencing reaction is complete, the different primer reactions may be combined and run as one sample, as long as each reaction used the same primer, (albeit distinctly labeled with a dye corresponding to A, C, G, or T). The above sequencing methods may be conducted by cycling or non-cycling methods.

High throughput sequencing may be used and is preferably conducted with an automated capillary electrophoresis (CE) system that separates labeled DNA molecules in a size-dependent manner such that signals corresponding to each nucleotide in a sequence are detected in a sequential fashion. For reviews of the use of CE in DNA sequencing and polymorphism analysis, see Heller, Electrophoresis 22:629-43, 2001; Dovichi et al., Methods Mol Biol 167:225-39, 2001; Mitchelson, Methods Mol Biol 162:3-26, 2001; and Dolnik, J Biochem Biophys Methods 41:103-19, 1999. An ABI PRISM® 3100 Genetic Analyzer used with an ABI PRISM 3100 capillary array, 36-cm (P/N#4315931) provides one useful commercial high throughput sequencing instrument using multi-color fluorescence and 16 capillaries operating in parallel. The MegaBACE™ 1000 DNA Analysis System (Molecular Dynamics, Inc and Amersham Pharmacia Biotech) and the 3700, or 3730-DNA Analyzers (Applied Biosystems) provide 48/96 capillary CE sequencers.

In certain aspects, methods are provided for amplifying a target segment of nucleotides for transcription and/or translation. In these aspects the one or more of the oligonucleotide primers may have an extender region that comprises a sequence encoding a promoter for an RNA polymerase (and in cases for translation, ribosome binding site, and if desired translation initiation codon). Preferably, the sequence encoding the promoter for an RNA polymerase is at or near the 5' terminus of the extender region. The distance between the sequence of the extender region encoding the promoter for the RNA polymerase and the 3' end of the complementary region can vary. The distance may be at least 30, or at least 40, or at least 50, or at least 60 nucleotides in length. The RNA polymerase promoter of the present invention may by an RNA polymerase promoter commonly used for sequencing reactions, such as SP6, T3 and T7. The length of the complimentary region and the extender region (excluding the sequence encoding a promoter for an RNA polymerase) can vary. In some embodiments, this length represents a contiguous segment of at least 50 nucleotides, or at least 60 nucleotides, or at least 80 nucleotides or at least 100 nucleotides. Transcription may be carried out using any methods known in the art, for example see Lingappa, et al., US patent application publication No. 20030153066. In some embodiments, the amplicon may be transcribed directly without an extra subcloning step. Alternatively the amplified nucleic acid may be cloned into a vector suitable for transcription using methods well known in the art. In certain embodiments, the transcription products can be further translated. Translation reactions can be carried out by any method known in the art, e.g., as described in Lingappa, J. R., et al., J. Cell. Biol. (1984) 125:99-111.

The invention will now be described in greater detail by reference to the following non-limiting examples.

Example 1

Sequencing of THRB Exon 3

Resistance to thyroid hormone (RTH) causes a variety of phenotypes which can include, high levels of protein-bound iodine, deaf-mutism, learning disabilities, mental retardation, delayed bone age, stunted growth, and stippled epiphyses. RTH can result from mutations in the exon 3 of the gene THRB, which encodes the thyroid hormone receptor-β. Exon 3 of THRB is only 22 nucleotides long and is flanked at the 5' and 3' directions by poly-T, poly-A and poly-G sequences which present barriers to obtaining the sequence of THRB exon 3. A polymorphism that interferes with dye-terminator sequencing reactions arises about 50 nucleotides upstream (5') of exon 3 in about 50% of patient samples.

To amplify THRB exon 3 in all patients and to obtain the nucleotide sequence of in individuals with this polymorphism, amplification primers were designed that hybridized to regions of THRB at a site between the polymorphic region and the repetitive elements. Specifically, the forward primer contained a complementary region at the 3' terminus of the primer designed to hybridize to a 21 nucleotide region of THRB immediately upstream of exon 3, and an extender region comprising 70 nucleotides that included a M13F primer hybridization site at the 5' end of the extender region. The reverse primer has a complementary region at the 3' terminus of the primer that was designed to hybridize to a region of THRB about 12 nucleotides downstream of exon 3 and an extender region that was 70 nucleotides in length and contained a M13R sequencing primer site at the 5' end.

Nucleic acid from patients suspected of carrying THRB gene mutations were amplified with the above primers. The resulting amplicon was approximately 200 nucleotides in length and contained the 22 nucleotides of THRB exon 3 flanked by the sequences corresponding to the extender regions of the respective amplification primers. The amplicon was sequenced using an ABI 3100 capillary sequencer in both the forward and reverse directions using M13F and M13R sequencing primers, respectively. While the first 50 nucleotides of the amplicon in both forward and reverse directions (corresponding to the extender region of the primer) were unreadable, the entire THRB exon 3 sequence was readable because the sequences corresponding to the exon were more than 50 nucleotides from the sequencing primer sites. The nucleotide sequences of THRB exon 3 were successfully obtained in both the forward and reverse directions in all patients studied.

Example 2

Sequencing of SDHB Exon 2

Mutations in the gene SDHB, a member of the succinate dehydrogenase gene family, have been linked to pheochromocytomas, tumors of the adrenal gland that secrete excess levels of epinephrine and norepinephrine. Poly-T and poly-A sequences occur in a region of the SDHB gene that is upstream (5') of the second exon, making sequencing exon 2 of SDHB difficult or impossible using traditional amplification and sequencing techniques.

Amplification of SDHB exon 2 is achieved using a forward amplification primer that contains a complementary region at the 3' terminus of the primer designed to hybridize to a region of the SDHB gene that is upstream of the second exon, yet downstream of the poly-T and poly-A sequences of the SDHB gene, and includes an extender region of at least 50 nucleotides in length that contains an M13 forward sequencing primer site at or near the 5' end of the primer. A reverse amplification primer is used that contains only a complementary sequence designed to hybridize at a site that is more than 50 nucleotides downstream of SDHB exon 2 and an M13R tail. The amplicon is sequenced in both directions by priming at the forward and reverse sequencing primer sites using a capillary sequencer.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

The invention claimed is:
1. A method for sequencing a target segment of nucleotides in a nucleic acid test sample, said method comprising:
  (a) amplifying said target segment of nucleotides using at least two oligonucleotide primers that flank the target segment, wherein at least one of the oligonucleotide primers comprise:
    i) a complementary region with a sequence of about 15 to about 25 nucleotides that hybridizes adjacent to the target segment of nucleotides; and
    ii) an extender region that includes a primer hybridization sequence wherein said extender region does not hybridize to the target segment of nucleotides and said extender region is not fully complementary to the segment of nucleotides adjacent to which the complementary region of the primer hybridizes in the target nucleic acids, with a proviso that the length of the complimentary region and the extender region excluding the primer hybridization sequence portion of the extender region together represents a contiguous segment of at least, or, about 50 nucleotides; and
  (b) determining the sequence of the amplified target segment by priming with an oligonucleotide primer that is complementary to said primer hybridization sequence of the extender region.

2. The method according to claim 1, wherein said target segment comprises less than, or, about 150 nucleotides.

3. The method according to claim 1, wherein said target segment comprises less than, or, about 50 nucleotides.

4. The method according to claim 1, wherein said target segment is a complete exon.

5. The method according to claim 1, wherein said target segment comprises exon 3 of the gene encoding the thyroid hormone receptor-β (THRB).

6. The method according to claim 1, wherein said target segment comprises exon 2 of the gene, SDHB, a member of the succinate dehydrogenase gene family.

7. The method according to claim 1, wherein said target segment of nucleotides is located in the nucleic acid less than 100 nucleotides away from a repetitive element, a loop, a bulge, a stem-loop structure, triplex DNA, tertiary or quaternary nucleic acid structure, an AT-rich region, a GC-rich region or a polymorphic region.

8. The method according to claim 1, wherein said primer hybridization sequence of the extender region is complementary to a primer used for nucleotide sequencing.

9. The method according to claim 1, wherein said primer hybridization sequence is complimentary to one or more primers selected from the group consisting of T7, T7 promoter, T7 terminator, T3, T3 promoter, M13, M13 forward (M13F), M13 reverse (M13R), and SP6.

10. The method according to claim 1, wherein said extender region is not complementary to the segment of nucleotides adjacent to which the complementary region of the primer hybridizes in the target nucleic acids.

11. The method according to claim 1, wherein said extender region does not hybridize under stringent conditions to said target nucleic acids.

12. The method according to claim 1, wherein said extender region is not subjected to cleavage by restriction enzymes.

13. The method according to claim 1, wherein said sequence of said amplified target segment is determined without a subcloning step.

14. The method according to claim 1, wherein said sequence of nucleic acids is determined by dye-termination sequencing methods.

15. A method for amplifying a target segment of nucleotides in a nucleic acid sample for nucleic acid sequence determination, said method comprising:
(a) contacting said nucleic acids in a test sample with at least two oligonucleotide primers that flank a target segment of nucleotides, wherein at least one of said oligonucleotide primers comprise:
i) a complementary region with a sequence of about 15 to about 25 nucleotides that hybridizes adjacent to the target segment of nucleotides; and
ii) an extender region that includes a primer hybridization sequence wherein said extender region does not hybridize to the target segment of nucleotides and said extender region is not fully complementary to the segment of nucleotides adjacent to which the complementary region of the primer hybridizes in the target nucleic acids, with a proviso that the length of the complimentary region and the extender region excluding the primer hybridization sequence portion of the extender region together represents a contiguous segment of at least, or, about 50 nucleotides; and
(b) amplifying said target segment of nucleotides by priming with said primers, wherein said target segment of nucleotides comprises up to, or, about 150 nucleotides and said target segment is located in the nucleic acid less than 100 nucleotides from a genomic region selected from the group consisting of a repetitive element, a loop, a bulge, a stem-loop structure, triplex DNA, tertiary or quanternary nucleic acid structure, AT-rich region, GC-rich region and polymorphic region, and wherein said complementary region of the primer hybridizes to the nucleic acid between said target segment and genomic region.

16. The method according to claim 15, wherein said extender region includes a primer hybridization sequence which can be used for sequencing by primer extension.

17. The method according to claim 16, wherein said primer hybridization sequence is complimentary to one or more primers selected from the group consisting of T7, T7 promoter, T7 terminator, T3, T3 promoter, M13, M13 forward (M13F), M13 reverse (M13R), and SP6.

18. The method according to claim 15, wherein said extender region does not hybridize under stringent conditions to said target nucleic acids.

19. The method according to claim 15, wherein said extender region is not complementary to the segment of nucleotides adjacent to which the complementary region of the primer hybridizes in the target nucleic acids.

20. The method according to claim 15, wherein said extender region is not subjected to cleavage by restriction enzymes.

21. The method according to claim 15, wherein said amplified target segment is sequenced.

22. The method according to claim 21, wherein said sequence of said amplified target segment is determined without a subcloning step.

23. The method according to claim 21, wherein said sequence of said amplified target segment is determined by dye-termination sequencing methods.

24. The method according to claim 15 wherein said target segment comprises less than, or, about 50 nucleotides.

25. The method according to claim 15, wherein said target segment is a complete exon.

26. The method according to claim 15, wherein said target segment comprises exon 3 of the gene encoding the thyroid hormone receptor-β (THRB).

27. The method according to claim 15, wherein said target segment comprises exon 2 of the gene, SDHB, a member of the succinate dehydrogenase gene family.

28. A method for amplifying a target segment of nucleotides in a nucleic acid sample for transcription of the amplified target segment, said method comprising:
(a) contacting a nucleic acid sample with at least two oligonucleotide primers that flank a target segment of nucleotides, wherein at least one of said oligonucleotide primers comprise:
i) a complementary region with a sequence of about 15 to about 25 nucleotides that hybridizes adjacent to the target segment of nucleotides; and
ii) an extender region that includes a sequence encoding a promoter for an RNA polymerase wherein said extender region does not hybridize to the target segment of nucleotides and said extender region is not fully complementary to the segment of nucleotides adjacent to which the complementary region of the primer hybridizes in the target nucleic acids, with a proviso that the length of the complimentary region and the extender region excluding the sequence encoding the promoter for an RNA polymerase portion of the extender region together represents a contiguous segment of at least, or, about 50 nucleotides; and (b) amplifying said target segment of nucleotides by priming with said primers, wherein said target segment of nucleotides comprises up to, or, about 150 nucleotides and said target segment is located in the nucleic acid less than 100 nucleotides from a genomic region selected from the group consisting of a repetitive element, a loop, a bulge, a stem-loop structure, triplex DNA, tertiary or quanternary nucleic acid structure, AT-rich region, GC-rich region and polymorphic region, and wherein said complementary region of the primer hybridizes to the nucleic acid between said target segment and genomic region.

29. The method according to claim 28, wherein said sequence encoding a promoter for an RNA polymerase is selected from the group consisting of SP6, T3 and T7.

30. The method according to claim 28, wherein said target segment comprises less than, or, about 50 nucleotides.

31. The method according to claim 28, wherein said target segment is a complete exon.

32. The method according to claim 28, wherein said target segment is a portion of a complete exon.

33. The method according to claim 28, wherein said target segment comprises exon 3 of the gene encoding the thyroid hormone receptor-β (THRB).

34. The method according to claim 28, wherein said target segment comprises exon 2 of the gene, SDHB, a member of the succinate dehydrogenase gene family.

35. The method according to claim 28, wherein said amplified target segment of nucleotides is contacted with an RNA polymerase to transcribe RNA.

36. The method according to claim 35, wherein said RNA is translated.

37. The method according to claim 28, wherein said amplified target segment of nucleotides is cloned into a vector for expression of an RNA or protein product encoded by said amplified target segment of nucleotides.

38. The method of claim 1, wherein the length of the complementary region and the extender region excluding the primer hybridization sequence together represents a contiguous segment of at least 50 nucleotides.

39. The method of claim 15, wherein the length of the complementary region and the extender region excluding the primer hybridization sequence together represents a contiguous segment of at least 50 nucleotides.

40. The method of claim 28, wherein the length of the complementary region and the extender region excluding the primer hybridization sequence together represents a contiguous segment of at least 50 nucleotides.

41. The method of claim 28, wherein the target segment of nucleotides comprises at least 150 nucleotides.

42. The method of claim 40, wherein the target segment of nucleotides comprises at least 150 nucleotides.

43. The method according to claim 1, wherein the contiguous segment is at least, or, about 60 nucleotides.

44. The method according to claim 1, wherein the contiguous segment is at least, or, about 80 nucleotides.

45. The method according to claim 1, wherein the contiguous segment is at least, or, about 100 nucleotides.

46. The method according to claim 15, wherein the contiguous segment is at least, or, about 60 nucleotides.

47. The method according to claim 15, wherein the contiguous segment is at least, or, about 80 nucleotides.

48. The method according to claim 15, wherein the contiguous segment is at least, or, about 100 nucleotides.

49. The method according to claim 28, wherein the contiguous segment is at least, or, about 60 nucleotides.

50. The method according to claim 28, wherein the contiguous segment is at least, or, about 80 nucleotides.

51. The method according to claim 28, wherein the contiguous segment is at least, or, about 100 nucleotides.

* * * * *

UNITED STATES PATENT AND TRADEMARK OFFICE
CERTIFICATE OF CORRECTION

| | | |
|---|---|---|
| PATENT NO. | : 7,585,626 B1 | Page 1 of 1 |
| APPLICATION NO. | : 10/921482 | |
| DATED | : September 8, 2009 | |
| INVENTOR(S) | : Feras Hantash and Jennifer Dianne Keen-Kim | |

It is certified that error appears in the above-identified patent and that said Letters Patent is hereby corrected as shown below:

IN THE CLAIMS

Column 15, line 46, replace "said nucleic acids in a test sample" with --nucleic acid sample--.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,585,626 B1 | Page 1 of 1 |
| APPLICATION NO. | : 10/921482 | |
| DATED | : September 8, 2009 | |
| INVENTOR(S) | : Hantash et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this

Twenty-third Day of November, 2010

David J. Kappos
*Director of the United States Patent and Trademark Office*